United States Patent
Swisher et al.

(10) Patent No.: US 10,130,770 B2
(45) Date of Patent: Nov. 20, 2018

(54) ENTERAL FEEDING SYRINGE ASSEMBLY

(71) Applicant: KPR U.S., LLC, Mansfield, MA (US)

(72) Inventors: David Rork Swisher, St. Charles, MO (US); Sandra Walker, St. Charles, MO (US); Timothy Eckenroth, Manchester, MO (US)

(73) Assignee: KPR U.S., LLC, Mansfield, MA (US)

( * ) Notice: Subject to any disclaimer, the term of this patent is extended or adjusted under 35 U.S.C. 154(b) by 93 days.

(21) Appl. No.: 15/174,315

(22) Filed: Jun. 6, 2016

(65) Prior Publication Data

US 2016/0361497 A1 Dec. 15, 2016

Related U.S. Application Data

(60) Provisional application No. 62/174,414, filed on Jun. 11, 2015.

(51) Int. Cl.
*A61M 5/31* (2006.01)
*A61M 39/10* (2006.01)
(Continued)

(52) U.S. Cl.
CPC .............. *A61M 5/31* (2013.01); *A61M 5/178* (2013.01); *A61M 39/10* (2013.01);
(Continued)

(58) Field of Classification Search
CPC ..... A61M 5/31; A61M 39/1011; A61M 39/10
See application file for complete search history.

(56) References Cited

U.S. PATENT DOCUMENTS 4,240,422 A * 12/1980 Hazen ................. A61M 5/347
604/241
4,390,017 A 6/1983 Harrison et al.
(Continued)

FOREIGN PATENT DOCUMENTS

EP 0462355 A1 12/1991
EP 0520618 A2 12/1992
(Continued)

OTHER PUBLICATIONS

PCT Notification of Transmittal of the International Search Report and the Written Opinion dated Sep. 6, 2016 in related international application PCT/US2016/036306, 13 pages.
(Continued)

*Primary Examiner* — Bradley J Osinski
(74) *Attorney, Agent, or Firm* — Adnan H. Bohri

(57) ABSTRACT

An enteral feeding syringe assembly includes a syringe including an engagement surface. A projecting connector portion extends from the engagement surface. A connector is configured for attachment to the syringe to connect the syringe to a fluid conduit or reservoir. The connector includes a male connector portion including a rim and a passage extending through the male connector portion. The projecting connector portion of the syringe is sized and shaped to be received in the male connector portion of the connector when the connector is attached to the syringe such that an exterior wall of the projecting connector portion sealingly engages the male connector portion within the passage of the male connector portion and the rim of the male connector portion engages the engagement surface of the syringe sealing the male connector portion around the projecting connector portion.

19 Claims, 11 Drawing Sheets

(51) Int. Cl.
*A61M 5/178* (2006.01)
*A61J 15/00* (2006.01)

(52) U.S. Cl.
CPC ...... *A61M 39/1011* (2013.01); *A61J 15/0026* (2013.01); *A61M 2005/3104* (2013.01); *A61M 2005/3106* (2013.01); *A61M 2005/3125* (2013.01); *A61M 2039/1033* (2013.01); *A61M 2039/1066* (2013.01)

(56) References Cited

U.S. PATENT DOCUMENTS

| | | | |
|---|---|---|---|
| 4,668,225 A | 5/1987 | Russo et al. | |
| 5,113,571 A | 5/1992 | Manska | |
| D340,111 S | 10/1993 | Yoshikawa | |
| 5,312,377 A * | 5/1994 | Dalton | A61M 39/10 285/331 |
| D381,075 S | 7/1997 | Manosalva et al. | |
| D401,325 S | 11/1998 | Hjertman et al. | |
| D440,304 S | 4/2001 | Morales | |
| 6,569,118 B2 * | 5/2003 | Johnson | A61M 5/347 604/164.04 |
| 6,699,233 B2 | 3/2004 | Slanda et al. | |
| 6,736,799 B1 | 5/2004 | Erbe et al. | |
| D492,030 S | 6/2004 | Rani | |
| D543,278 S | 5/2007 | Numata et al. | |
| 7,316,669 B2 * | 1/2008 | Ranalletta | A61M 5/3134 604/199 |
| D578,210 S | 10/2008 | Muta et al. | |
| 8,016,809 B2 | 9/2011 | Zinger et al. | |
| 8,287,518 B2 | 10/2012 | Kitani et al. | |
| 8,348,902 B2 | 1/2013 | Sugita et al. | |
| 8,454,564 B2 | 6/2013 | Deppisch et al. | |
| 8,479,370 B2 | 7/2013 | Grant | |
| 8,628,509 B2 | 1/2014 | Kropczynski, Jr. et al. | |
| D700,318 S | 2/2014 | Amoah et al. | |
| D728,780 S | 5/2015 | Pieroni et al. | |
| D728,781 S | 5/2015 | Pierson et al. | |
| D729,931 S | 5/2015 | Takeuchi et al. | |
| D733,870 S | 7/2015 | Broyles et al. | |
| D739,524 S | 9/2015 | Zemel et al. | |
| D739,933 S | 9/2015 | Ettlin | |
| 9,126,014 B2 | 9/2015 | Yamoto et al. | |
| D741,476 S | 10/2015 | Hiraoka et al. | |
| D743,025 S | 11/2015 | Berler | |
| D747,473 S | 1/2016 | Martin et al. | |
| D747,797 S | 1/2016 | Fourt et al. | |
| D748,777 S | 2/2016 | Uenishi et al. | |
| 9,283,148 B2 | 3/2016 | Hyun et al. | |
| D754,331 S | 4/2016 | Wargner et al. | |
| 2006/0033334 A1 | 2/2006 | Weber et al. | |
| 2006/0047251 A1 | 3/2006 | Bickford Smith et al. | |
| 2006/0106349 A1 | 5/2006 | Kito et al. | |
| 2007/0076401 A1 | 4/2007 | Carrez et al. | |
| 2007/0129705 A1 * | 6/2007 | Trombley, III | A61M 39/10 604/523 |
| 2008/0045929 A1 | 2/2008 | Birnbach | |
| 2008/0140055 A1 | 6/2008 | Shirley | |
| 2012/0150129 A1 | 6/2012 | Jin et al. | |
| 2012/0245564 A1 | 9/2012 | Tekeste et al. | |
| 2012/0330238 A1 | 12/2012 | Robert et al. | |

FOREIGN PATENT DOCUMENTS

| | | |
|---|---|---|
| WO | 91-05581 A1 | 5/1991 |
| WO | 2007-103998 A2 | 9/2007 |
| WO | 2007-131086 A2 | 11/2007 |

OTHER PUBLICATIONS

American National Standard Institute, "Small-bore connectors for liquids and gases in healthcare applications—Part 3: Connectors for enteral applications", Published by: Association for the Advancement of Medical Instrumentation 4301 N. Fairfax Drive, Suite 301 Arlington, VA 22203-1633 www.aami.org, © ISO/IEC 2013—All rights reserved, AAMI/ISO 80369-3, 43 pages.
Office Action dated Aug. 3, 2016 in related U.S. Appl. No. 29/530,000, 10 pages.
Office Action dated Sep. 8, 2017 in related U.S. Appl. No. 29/529,998, 9 pages.
"Alternate Syringes: Low Displacement Option," Rork Swisher, ISO 80369 Series Meeting, Berlin, Germany, Mar. 19, 2014, 11 pages.

* cited by examiner

ENTERAL FEEDING SYRINGE ASSEMBLY

CROSS-REFERENCE TO RELATED APPLICATION

This application claims the benefit of priority under 35 U.S.C. § 119 to U.S. Patent Application No. 62/174,414, titled ENTERAL FEEDING SYRINGE ASSEMBLY, which was filed on Jun. 11, 2015, and which is incorporated herein by reference in its entirety for all purposes.

FIELD

The present disclosure generally relates to an enteral feeding syringe assembly.

BACKGROUND

In a medical environment, many devices have tubing or other fluid conduits adapted for manual connection in order to provide a fluid connection between devices or between a device and a patient including enteral feeding pumps and enteral feeding lines. For example, enteral feeding or delivery of medicines to the gastrointestinal tract may be accomplished by connecting an enteral feeding connector to an oral syringe. Some patients, including particularly neo-natal patients, are best served by a high degree of accuracy in the volume of fluid delivered to the patient. Each of these devices includes one or more connectors that a user or practitioner may connect together.

FIG. 1 shows a conventional enteral feeding connector assembly including a male enteral feeding connector 1 and a female enteral feeding connector 3 configured to be connected to one another for use in connecting enteral fluid lines in healthcare applications. The female enteral feeding connector 3 receives a male connector portion 1A of the male enteral feeding connector 1 within an interior space 5. An exterior surface of the male connector portion 1A engages and seals with an interior surface of the female enteral feeding connector 3 to achieve a fluid-tight connection. The enteral feeding connectors 1, 3 may then deliver fluid in the fluid lines through a fluid passage 7 extending through the connectors. Fluid is typically delivered from the female connector 3 to the male connector 1. A dead space 9 is located adjacent an inlet of the male enteral feeding connector 1. The dead space 9 defines an area of the interior space 5 in the female enteral feeding connector 3 that is not occupied by the portion of the male enteral feeding connector 1 received therein. A problem with having this dead space is that fluid intended for delivery can pool within the dead space causing an under dose of fluid to be delivered to the patient. Conversely, the pooled fluid may not be accounted for in the fluid measurement resulting in an overdose of fluid to the patient. Although errors may be small, they can be important for certain patients, such as neo-natal infants.

SUMMARY

In one aspect, an enteral feeding syringe assembly generally comprises a syringe including an engagement surface. A projecting connector portion extending from the engagement surface. An interior chamber is disposed within the syringe. The projecting connector portion includes an exterior circumferential wall and a fluid passage extending through the projecting connector portion. The fluid passage is in fluid communication with the interior chamber of the syringe. A connector is configured for attachment to the syringe to connect the syringe to a fluid conduit or reservoir. The connector comprises a male connector portion including a rim and a passage extending through the male connector portion. The projecting connector portion of the syringe is sized and shaped to be received in the male connector portion of the connector when the connector is attached to the syringe such that the exterior wall of the projecting connector portion sealingly engages the male connector portion within the passage of the male connector portion and the rim of the male connector portion engages the engagement surface of the syringe sealing the male connector portion around the projecting connector portion.

In another aspect, an enteral feeding syringe generally comprises a barrel and a projecting connector portion extending from the barrel. A shroud extends around the projecting connector portion. An interior chamber is disposed within the barrel. The projecting connector portion includes an exterior circumferential wall and a fluid passage extending through the projecting connector portion. The fluid passage is in fluid communication with the interior chamber of the barrel. The shroud defines an opening that exposes the projecting connector portion.

BRIEF DESCRIPTION OF THE DRAWINGS

Corresponding reference characters indicate corresponding parts throughout the drawings.

DETAILED DESCRIPTION OF THE DRAWINGS

Figure 1:
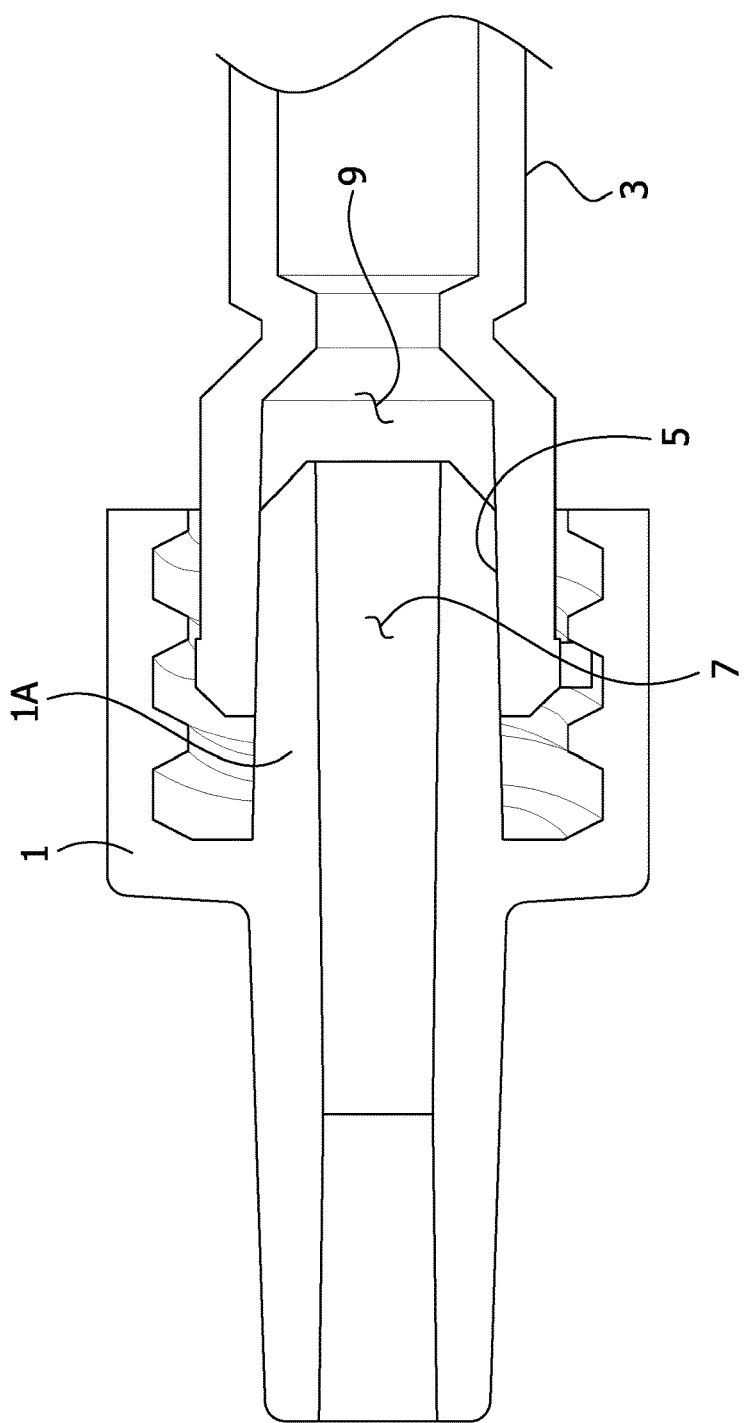
FIG. 1 is a longitudinal section of a prior art enter feeding
Figure 2:
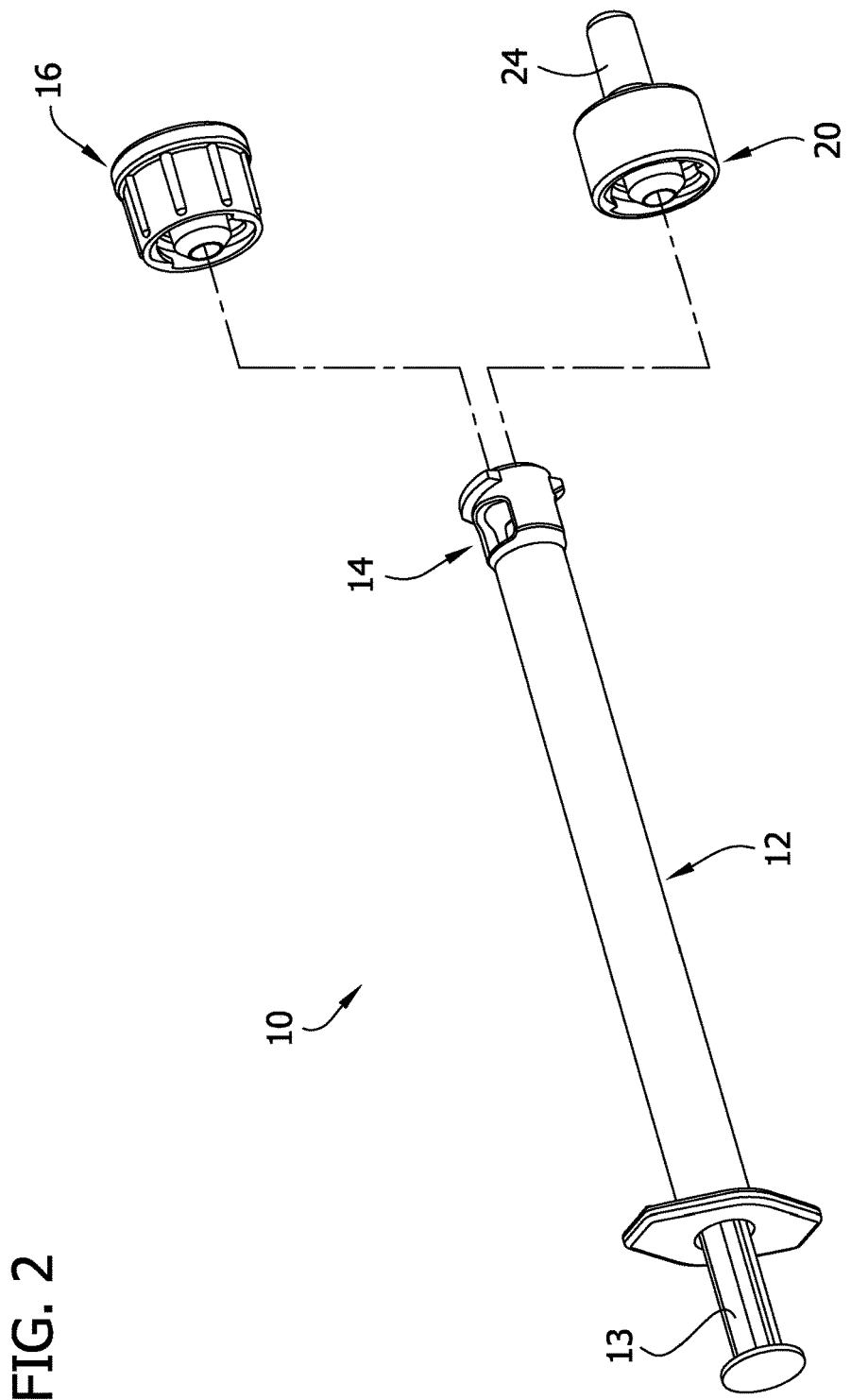
FIG. 2 is an exploded view of an enteral feeding syringe assembly.
Figure 3:
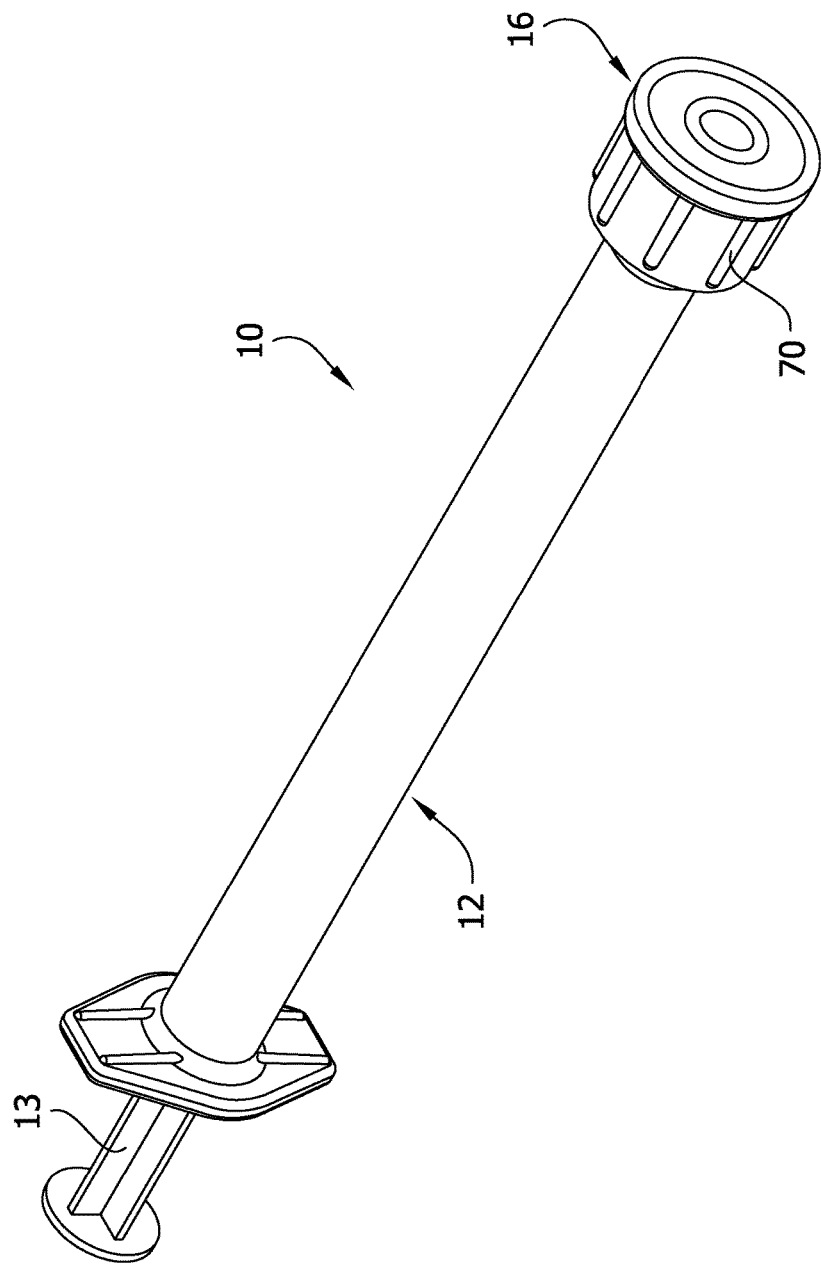
FIG. 3 is a perspective of the enteral feeding syringe assembly showing a cap attached to a syringe of the assembly.

Referring to FIGS. 2-6, an enteral feeding syringe assembly is generally indicated at 10. The syringe assembly is configured to fluidly connect to a fluid conduit (e.g., a feeding tube) or a reservoir (e.g., medical tubing, bottle, nutrient bag, etc.) for retrieving fluid from the fluid reservoir or delivering fluid to a subject through the fluid conduit. The syringe assembly 10 comprises a syringe 12 including a female fitting 14 on a distal end of the syringe for connecting to a complementary male connector. The assembly 10 may further comprise a cap 16 including a male connector portion 18 (FIG. 4) for providing a sealed connection with the female fitting 14 of the syringe 12 when the cap is secured (e.g., threaded) onto the syringe. Alternatively, an enteral feeding connector 20 may include a male connector portion 22 (FIG. 6) for providing a sealed connection with the female fitting 14 on the syringe 12 when the enteral feeding connector is secured (e.g., threaded) onto the female fitting of the syringe. When the enteral feeding connector 20 is properly secured to the syringe 12, a tube connector portion 24 of the enteral feeding connector can be connected to a fluid conduit or reservoir to fluidly connect the syringe to the fluid conduit or reservoir. A plunger 13 can be received in a barrel of the syringe 12 and used to discharge fluid from the syringe and to draw fluid into the syringe. In the illustrated embodiment, the female fitting 14 is formed integrally with a remainder of the syringe 12. However, the female fitting 14 could be formed separately from the syringe 12 and suitably attached to the syringe.

Figure 7:
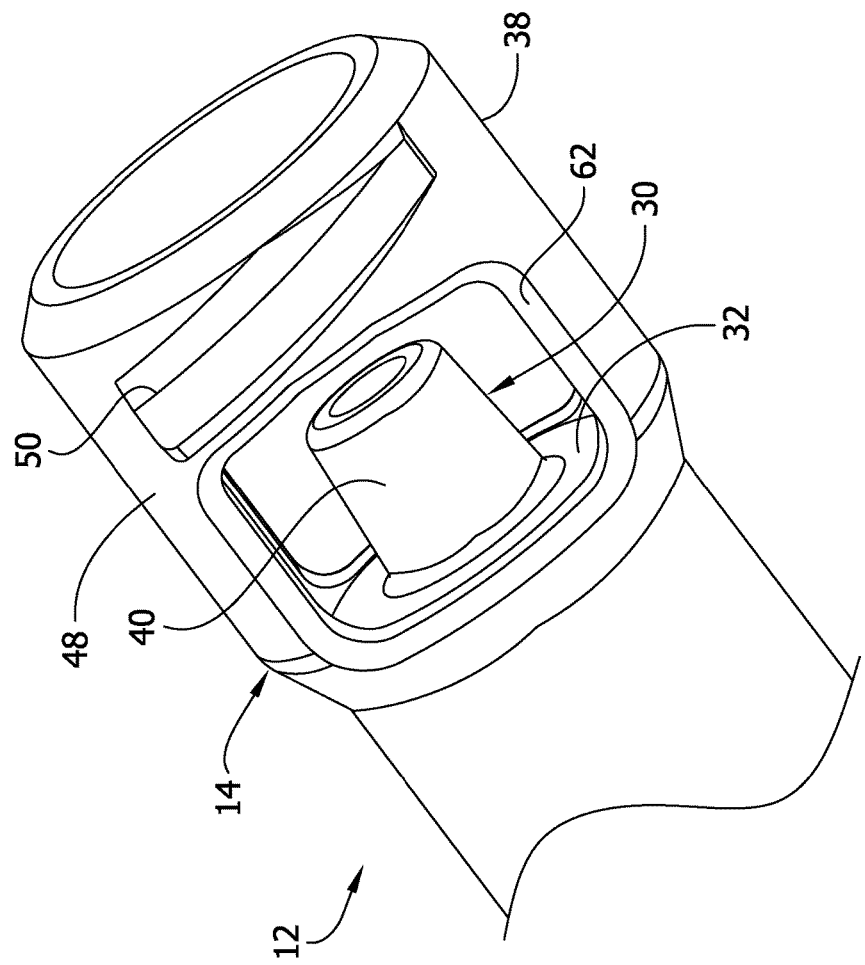
FIG. 7 is an enlarged fragmentary perspective of the syringe.
Figure 8:
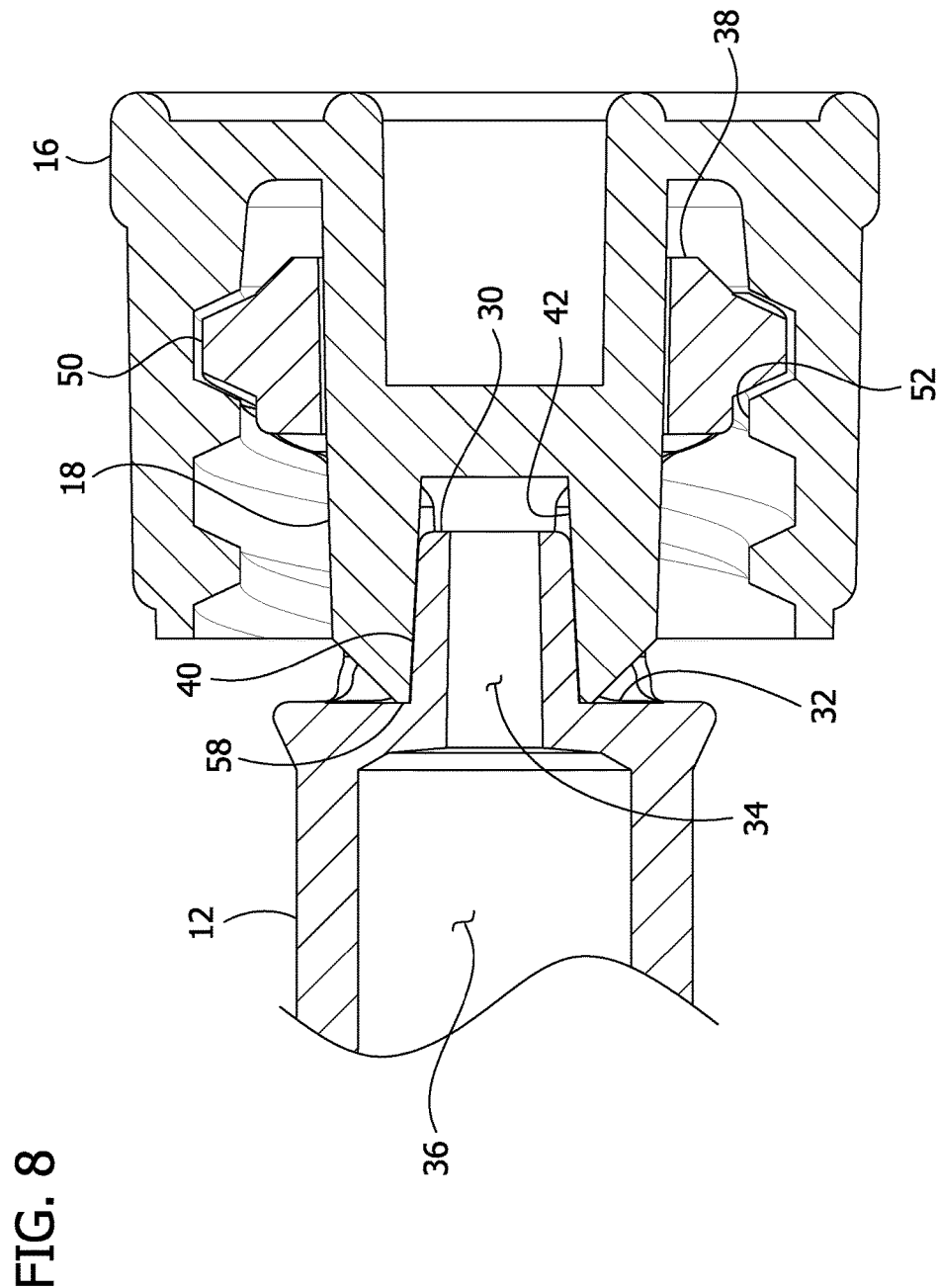
FIG. 8 is an enlarged fragmentary elevation of a portion of FIG. 3.
Figure 9:
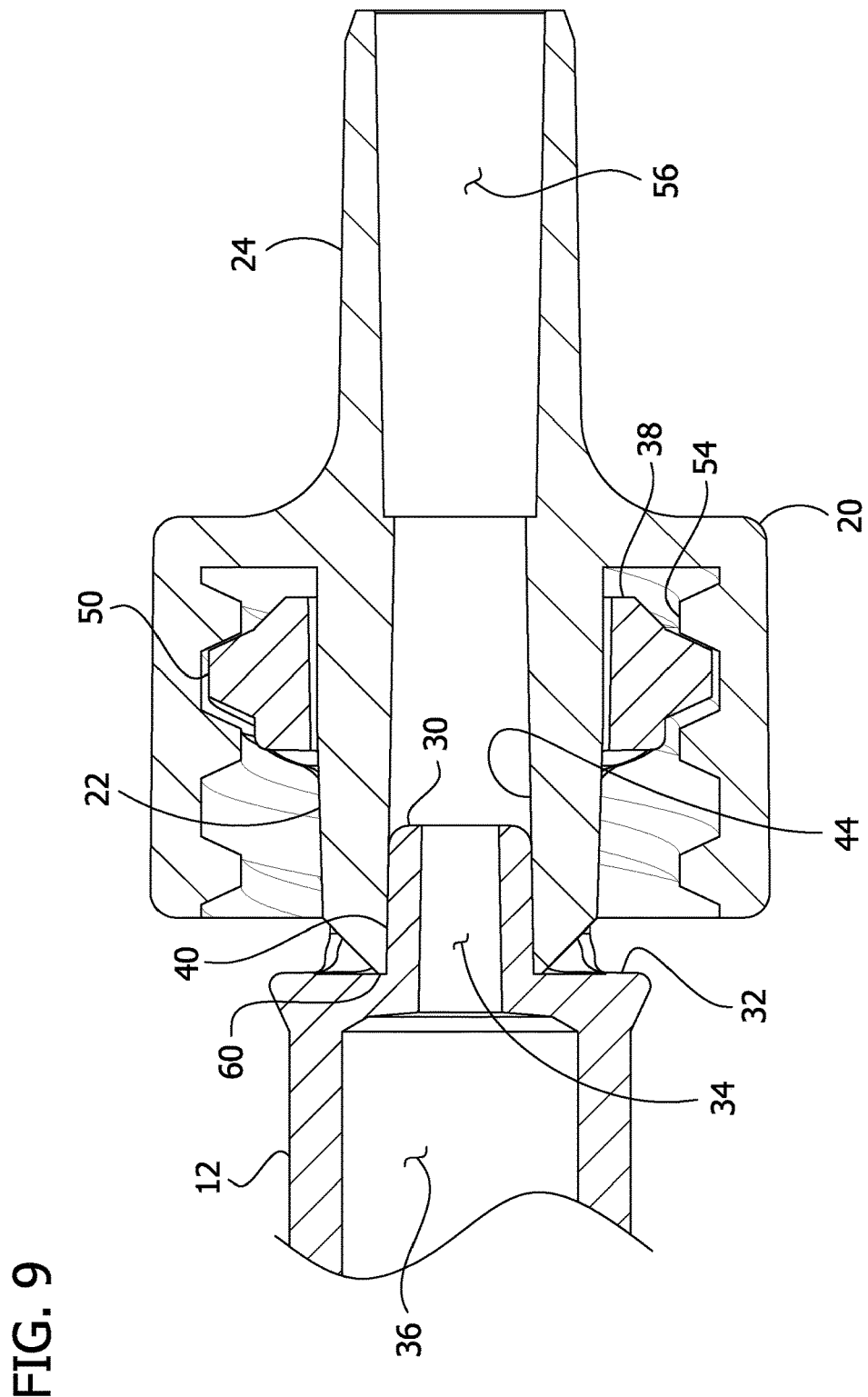
FIG. 9 is an enlarged fragmentary elevation of a portion of FIG. 5.
Figure 10:
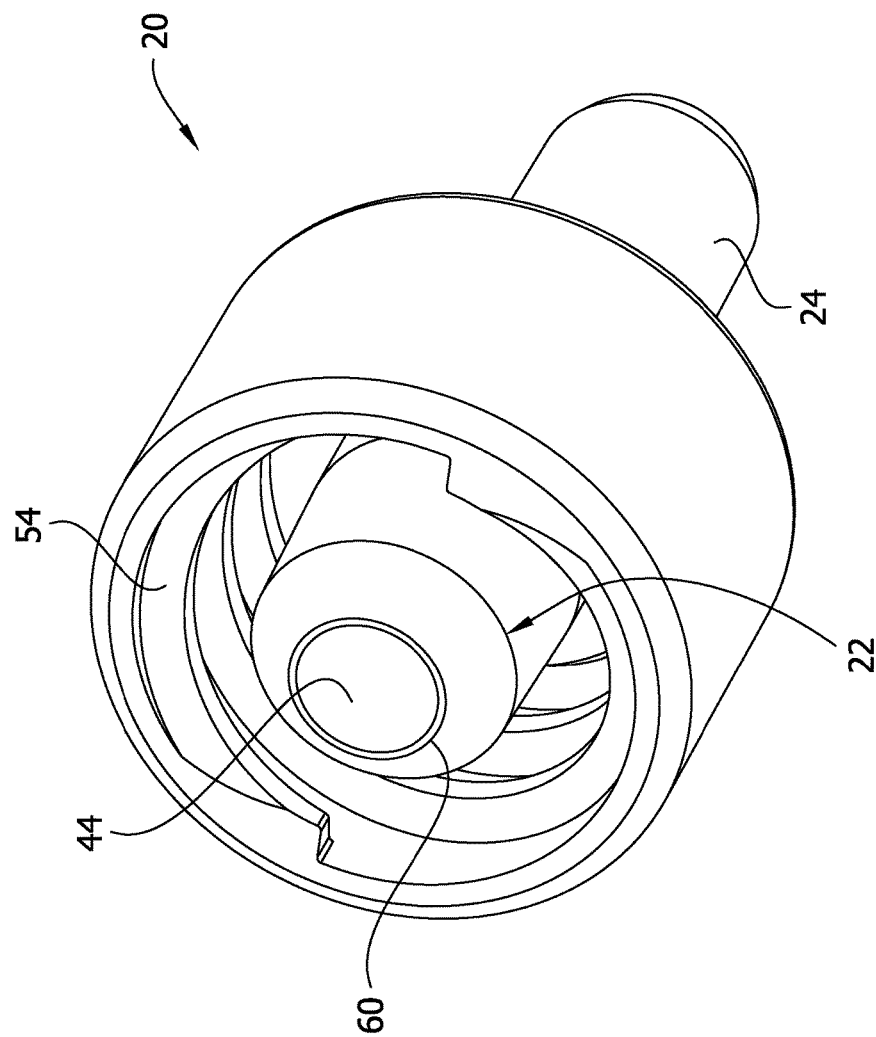
FIG. 10 is a perspective of the enteral feeding connector.

Referring to FIG. 8, the female fitting 14 of the syringe 12 may comprise a projecting connector portion 30 extending from a floor 32 (broadly, "engagement surface") surrounding the projecting connector portion. The floor 32 may extend circumferentially around the entirety of the projecting connector portion 30 and faces axially outward from the syringe. A fluid passage 34 may extend through the projecting connector portion 30 from an open distal end of the projecting connector portion to an interior chamber 36 of the syringe 12. A connector shroud 38 may extend around the projecting connector portion 30. The shroud 38 of the female fitting 14 may include openings 62 (FIG. 7), which help to prevent intake of air into the interior chamber 36 of the syringe. Air inside the shroud 38 that is displaced by the female fitting 14 when it enters the shroud to make a fluid connection can exit the shroud through the openings 62, rather than being forced into the syringe 12. Keeping air out of the syringe 12 is desirable. The projecting connector portion 30 of the female fitting prior to connecting the cap 16 or enteral feeding connector 20 to the syringe 12 is visible through the opening. Similarly, the connection of the projecting connector portion 30 to the male connector portion 22 of the enteral feeding connector 20, or to the male connector portion 18 of the cap 16 are visible from the side of the female fitting 14 through the openings 62. Each opening 62 may extend generally from a location adjacent the floor 32 of the female fitting 14 past a distal tip of the projecting connector portion 30 exposing an entire length of the projecting connector portion through the opening. In the illustrated embodiment, there are two openings 62. However, other numbers of openings 62 are within the scope of the present disclosure. Further, it is envisioned that the openings 62 could be omitted without departing from the scope of the present disclosure.

A circumferential side wall 40 of the projecting connector portion 30 may be configured for sealing engagement with respective inner surfaces 42, 44 of the male connector portions 18, 22 of the cap 16 and enteral feeding connector 20, respectively (FIGS. 8-11). For instance, the circumferential side wall 40 of the projecting connector portion 30 may have a continuous profile such that the projecting connector portion is free of any channels or grooves in the outer surface of the projecting connector portion. The projecting connector portion 30 may taper from the floor 32 of the female fitting 14 to a distal end of the projecting connector portion. An outer surface 48 of the connector shroud 38 may include threads 50 for engaging threads 52 on an inner surface of the cap 16, or threads 54 on an inner surface of the enteral feeding connector 20 for securely engaging the female fitting 14 with either the cap or the enteral feeding connector. The circumferential side wall 40 of the projecting connector portion 30 engages and seals with an interior surface of inner surface 42 of the male connector 18 when the cap 16 is attached, or engages and seals with the inner surface 44 of the male connector portion 22 of the feeding connector 20 depending upon whether the cap or feeding connector is connected to the syringe 12. In addition, a rim 58 of the male connector portion 18 of the cap 16, and a rim 60 of the male connector portion 22 of the enteral feeding connector 20 may engage and seal with the floor 32 of the female fitting 14 of the syringe 12 when either the cap or the enteral feeding connector are attached to the syringe. Connection of the female fitting 14 to the male connector portion 22 of the enteral feeding connector 20 establishes fluid communication between the fluid passage 34 in the syringe 12 and a fluid passage 56 in the enteral feeding connector for placing the interior chamber 36 of the syringe 12 in fluid communication with a fluid conduit or reservoir connected to the tube connector portion 24 of the enteral feeding connector. Moreover, the engagement between the female fitting 14 of the syringe 12 and the male connector portion 22 of enteral feeding connector 20 provides both a sealed connection along the circumferential side wall 40 of the projecting connector portion 30 with the inner surface 44 of the male connector portion 22 and a sealed connection extending around the projecting connector portion along the floor 32 of the female fitting. Thus, a sealed connection is established along two separate surfaces of the female fitting 14. Therefore, a fluid tight connection is ensured when the enteral feeding connector 20 is attached to the syringe 12. It will be appreciated that the sealing reception of the projecting connector portion 30 in the fluid passage 56 effectively reverses the male/female connection of the prior art (FIG. 1). However, the present invention provides additional sealing by sealing engagement of the rim 58 with the floor 32.

Figure 4:
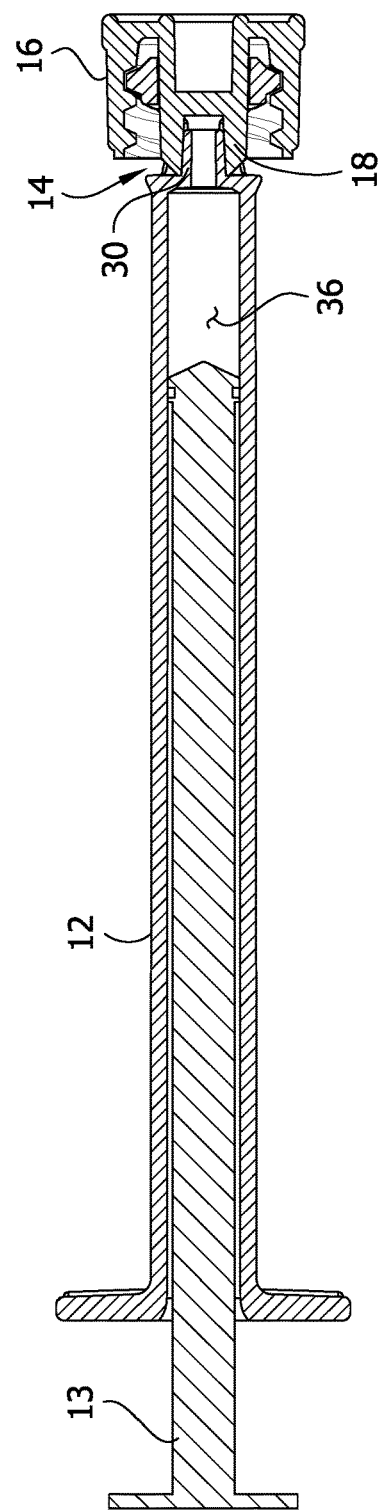
FIG. 4 is a longitudinal section of the assembly of FIG. 2.
Figure 5:
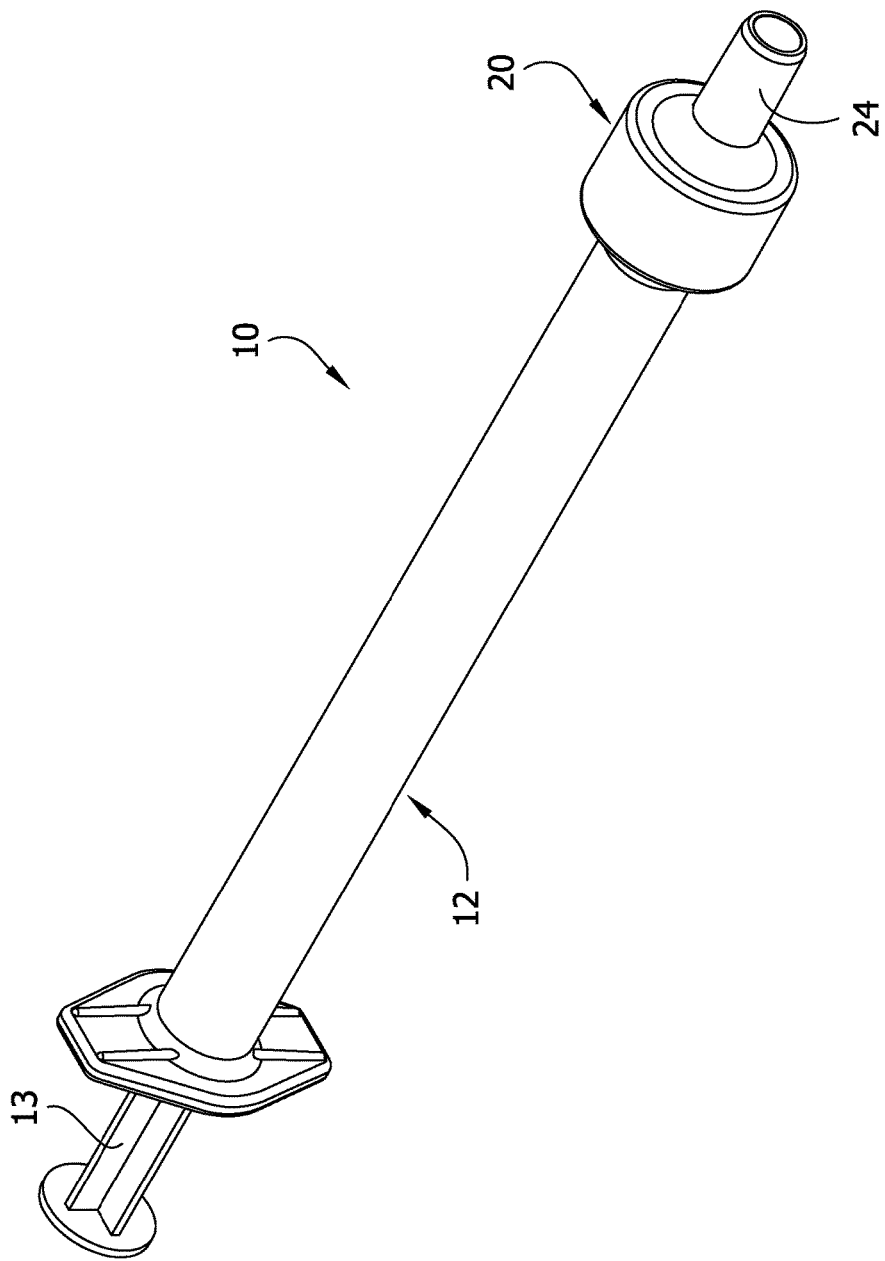
FIG. 5 is a perspective of the enteral feeding syringe assembly showing an enteral feeding connector attached to the syringe of the assembly.
Figure 6:
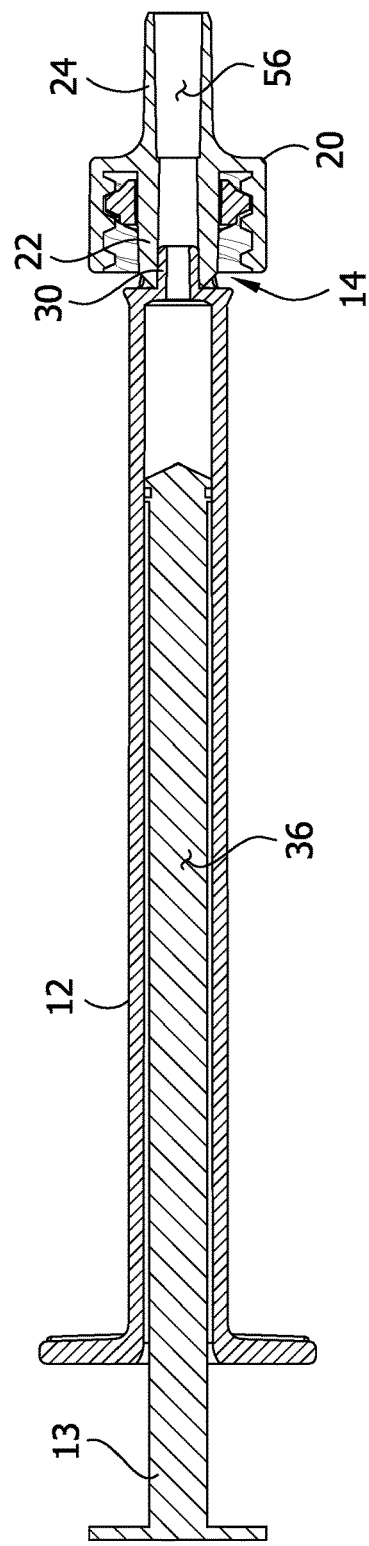
FIG. 6 is a longitudinal section of the assembly of FIG. 4.
Figure 11:
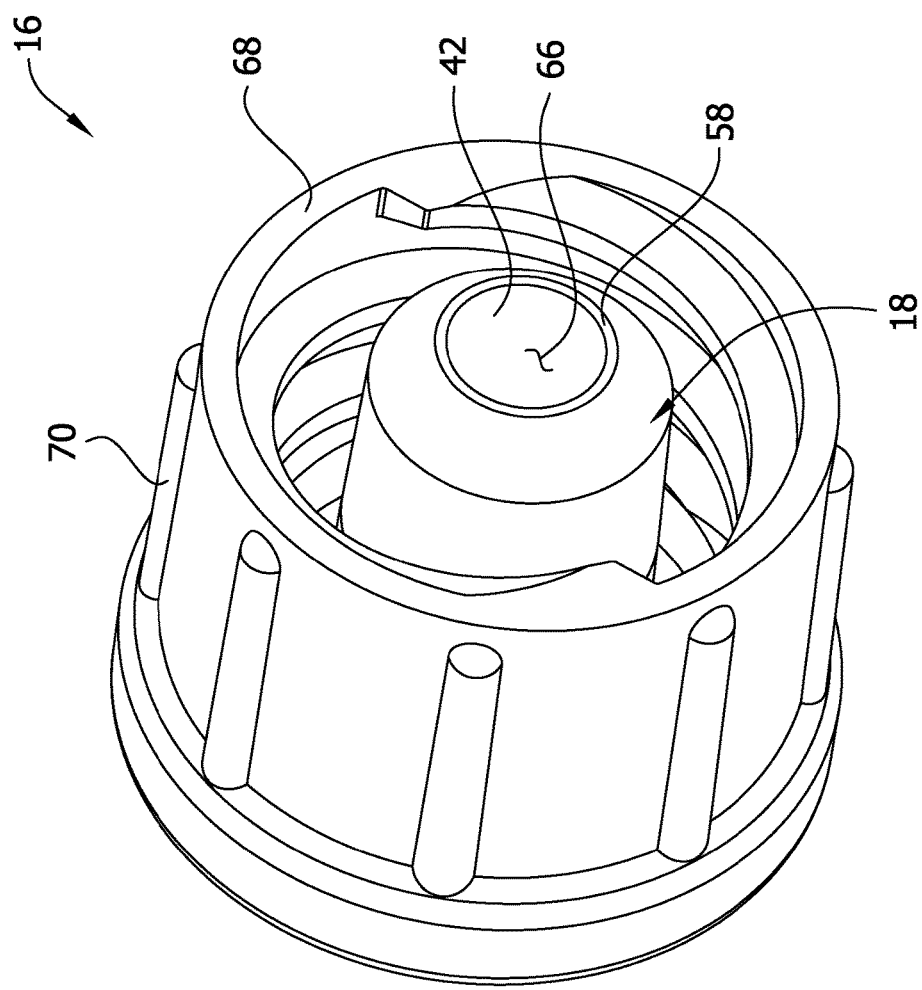
FIG. 11 is a perspective of the cap.

Referring to FIGS. 4, 8, and 11, the cap 16 may comprise the male connector portion 18 including a passage 66 extending through the male connector portion, and an annular portion 68 surrounding the male connector portion. The cap 16 may include a grip portion 70 (FIGS. 3 and 11) for manipulating the cap. The cap 16 is configured to cover the female fitting 14 of the syringe 12 and block the fluid passage 34 of the projecting connector portion 30 when the enteral feeding syringe assembly 10 is not being used. When it is desired to use the enteral feeding syringe assembly 10, the cap 16 can be removed from the female fitting 14 of the syringe 12 and the enteral feeding connector 20 can be attached to the female fitting.

In use, the enteral feeding syringe assembly 10 places the syringe 12 in fluid communication with a fluid reservoir for retrieving fluid from the fluid reservoir. Alternatively, the enteral feeding syringe assembly 10 can place the syringe 12 in fluid combination with a fluid conduit to deliver fluid to the fluid conduit. The engagement between the female fitting 14 of the syringe 12 and the male connector portion 22 of enteral feeding connector 20 ensures that a fluid tight connection is produced when the enteral feeding connector is attached to the syringe. No portion of the syringe volume is occupied by a mating connector. Therefore the volume of fluid in the syringe is always constant, even after connection to the enteral feeding connector is made.

Having described embodiments of the invention in detail, it will be apparent that modifications and variations are possible without departing from the scope of the invention defined in the appended claims.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An enteral feeding syringe comprising a barrel, a projecting connector portion extending from the barrel, a shroud extending from the barrel around the projecting connector portion, and an interior chamber disposed within the barrel, the shroud being defined by a circumferentially extending side wall and an axially facing end wall, the projecting connector portion including an exterior circumferential wall and a fluid passage extending through the projecting connector portion, the fluid passage being in fluid communication with the interior chamber of the barrel, the shroud defining an opening in the circumferentially extending side wall exposing the projecting connector portion, the opening being bounded on all sides by the shroud.

2. The syringe of claim 1, wherein the opening has a height and the projecting connector portion has a length, the height of the opening being greater than the length of the projecting connector portion such that an entirety of the length of the projecting connector portion is exposed through the opening.

3. The syringe of claim 1, wherein the shroud comprises a threaded outer surface for mating with threads on a connector.

4. The syringe of claim 1, wherein the projecting connector portion includes a free end, the shroud extending axially past the free end of the projecting connector portion.

5. The syringe of claim 1, wherein the opening comprises a first opening, the syringe further comprising a second opening in the circumferentially extending side wall.

6. The syringe of claim 5, wherein the second opening is diametrically opposed to the first opening.

7. An enteral feeding syringe assembly comprising:
a syringe including an engagement surface, a projecting connector portion extending from the engagement surface, a shroud extending around the projecting connector portion, and an interior chamber disposed within the syringe, the projecting connector portion including an exterior circumferential wall and a fluid passage extending through the projecting connector portion, the fluid passage being in fluid communication with the interior chamber of the syringe; and
a connector configured for attachment to the syringe to connect the syringe to a fluid conduit or reservoir, the connector comprising a male connector portion including a rim and a passage extending through the male connector portion,
the projecting connector portion of the syringe being sized and shaped to be received in the male connector portion of the connector when the connector is attached to the syringe such that the exterior wall of the projecting connector portion sealingly engages the male connector portion within the passage of the male connector portion and the rim of the male connector portion engages the engagement surface of the syringe sealing the male connector portion around the projecting connector portion;
wherein the male connector portion of the connector includes a circumferentially extending outer surface free of contact with an interior surface of the shroud when the connector is attached to the syringe, the interior surface of the shroud being free of threads.

8. The assembly of claim 7, wherein the engagement surface extends circumferentially around the projecting connector portion.

9. The assembly of claim 7, wherein the engagement surface faces axially outward of the syringe.

10. The assembly of claim 7, wherein the shroud comprises a threaded outer surface for mating with threads on the connector.

11. The assembly of claim 7, further comprising an opening in the shroud, a height of the opening being greater than a length of the projecting connector portion such that an entirety of the length of the projecting connector portion is exposed through the opening.

12. The assembly of claim 7, wherein the connector comprises a tube connector portion integrally formed with the male connector portion and configured for connecting to a medical tube.

13. The assembly of claim 7, further comprising a cap for attachment to the syringe to cover the fluid passage in the projecting connector portion of the syringe, the cap comprising a male connector portion including a rim, the male connector portion of the cap receiving the projecting connector portion of the syringe when the cap is attached to the syringe such that the rim of the male connector portion of the cap engages the engagement surface of the syringe sealing the male connector portion of the cap around the projecting connector portion.

14. The assembly of claim 7 wherein the connector further comprises a skirt defining an inner surface extending around and radially spaced from the male connector portion.

15. The assembly of claim 14 wherein the inner surface of the skirt has threads thereon.

16. An enteral feeding syringe assembly comprising:
a syringe including an engagement surface, a projecting connector portion extending from the engagement surface, and an interior chamber disposed within the syringe, the projecting connector portion including an exterior circumferential wall and a fluid passage extending through the projecting connector portion, the fluid passage being in fluid communication with the interior chamber of the syringe; and
a connector configured for attachment to the syringe to connect the syringe to a fluid conduit or reservoir, the connector comprising a male connector portion including a rim and a passage extending through the male connector portion,
the projecting connector portion of the syringe being sized and shaped to be received in the male connector portion of the connector when the connector is attached to the syringe such that the exterior wall of the projecting connector portion sealingly engages the male connector portion within the passage of the male connector portion and the rim of the male connector portion engages the engagement surface of the syringe sealing the male connector portion around the projecting connector portion;
the syringe further including a shroud extending around the projecting connector portion, the shroud defining an opening in a circumferentially extending side wall of the shroud exposing the projecting connector portion, the opening being bounded on all sides by the shroud.

17. The assembly of claim 16, wherein the opening comprises a first opening, the syringe further comprising a second opening in the circumferentially extending side wall.

18. The assembly of claim 17, wherein the second opening is diametrically opposed to the first opening.

19. The assembly of claim 16, wherein the male connector portion of the connector includes a circumferentially extending outer surface free of contact with an interior surface of the shroud, the interior surface of the shroud being free of threads.

\* \* \* \* \*